(12) United States Patent
Chang et al.

(10) Patent No.: US 7,534,569 B2
(45) Date of Patent: May 19, 2009

(54) METHOD OF GENERATING LONG NUCLEIC ACID MOLECULES OF DEFINED SEQUENCE

(75) Inventors: Chu-An Chang, Piedmont, CA (US); Shiaw-Min Chen, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 11/770,787

(22) Filed: Jun. 29, 2007

(65) Prior Publication Data

US 2007/0254343 A1    Nov. 1, 2007

Related U.S. Application Data

(63) Continuation of application No. 10/819,656, filed on Apr. 7, 2004, now abandoned.

(60) Provisional application No. 60/462,282, filed on Apr. 11, 2003.

(51) Int. Cl.
    *C12Q 1/66*    (2006.01)
    *C07H 21/02*   (2006.01)
    *C07H 21/04*   (2006.01)

(52) U.S. Cl. .................. 435/6; 536/23.1; 536/24.33

(58) Field of Classification Search ................ None
    See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,503,995 A * | 4/1996 | Khudyakov et al. | ........ 435/91.1 |
| 5,538,848 A | 7/1996 | Livak et al. | |
| 5,856,092 A | 1/1999 | Dale et al. | |
| 5,928,907 A | 7/1999 | Woudenberg et al. | |
| 6,015,674 A | 1/2000 | Woudenberg et al. | |
| 6,210,891 B1 | 4/2001 | Nyren et al. | |
| 6,218,118 B1 | 4/2001 | Sampson et al. | |
| 6,248,521 B1 * | 6/2001 | Van Ness et al. | ................ 435/6 |
| 6,368,834 B1 | 4/2002 | Senapathy et al. | |
| 6,448,407 B1 | 9/2002 | Lee et al. | |
| 6,660,229 B2 | 12/2003 | Cantor et al. | |
| 6,777,189 B2 | 8/2004 | Wei et al. | |
| 2001/0049125 A1 | 12/2001 | Stemmer et al. | |
| 2002/0119535 A1 | 8/2002 | Slater et al. | |
| 2003/0219792 A1 * | 11/2003 | Armes et al. | .................. 435/6 |
| 2004/0170968 A1 | 9/2004 | Lizardi | |
| 2004/0171041 A1 | 9/2004 | Dahl et al. | |

FOREIGN PATENT DOCUMENTS

JP          09149789 A    6/1997
WO          WO-00/46232 A    8/2000

OTHER PUBLICATIONS

Cello, J. et al; Chemical synthesis of poliovirus cDNA: generational infectious virus in the absence of natural teaplate; Science; 297, pp. 1016-1018; 2002.
Chidgeavadze, J. et al.; 2', 3'-Dideoxy-3', Aminucleoside 5'-Triphosphates are the Terminators of DNA Synthesis Catalyzed by DNA Polymers; Nucleic Acids Research; vol. 12, No. 3, pp. 1671-1686; 1984.
Chidgeavadze, Z et al., Nucleoside 5'-Triphosphates With Modified Sugars as Substrates; Biochem. Biophys. Acta; 868, pp. 145-152; 1986.
Chidgeavadze, Z. et al., 3'-Fluoro-2', 3'-Dideoxyribonucleoside 5'-Triphosphates: Terminators of DNA Syntheses; FEBS Lett.; vol. 183, pp. 275-278; 1985.
Clark, James M,; Novel Non-Templated Nucleotide Addition Reactions Catalyzed by Procaryotic and Eudaryotic DNA Polymerases; Nucleic Acids Research; vol. 16, No. 20; pp. 9677-9686; 1988.
Derwent Abstract and Machine Translation of JP 09149789 A (7 pp).
Dyatkina, N. et al.; Properties of 2', 3'-Dideoxy-2', 3'-Dehydrothymidine 5'-Triphosphate in Terminating DNA Synthesis Catalyzed by Several Different DNA Polymerases; FEBS Lett.; vol. 219, No. 1, pp. 151-155; 1987.
Haas, Stefan A. et al.; Genome-scale design of PCR primers and long oligomers for DNA microarrays; Nucleic Acids Research; vol. 31, No. 19; pp. 5576-5581; 2003.
Instructions for Pierce Reacti-Gel CDI Supports (2 pp).
Magnuson, et al.; Substrate Nucleotide-Determined Non-Templated Addition of Adenine by Taq DNA Polymerase: Implications for PCR-Based Genotyping and Cloning; BioTechniques; vol. 21, No. 4; pp. 700-709; Oct. 1996.
Martinez, C. et al.; An Allylic/Acyclic Adenosine Nucleoside Triphosphate for Termination of DNA Synthesis by DNA Template-Dependent Polymerases; Nucleic Acids Research; vol. 27, No. 5, pp. 1271-1274; 1999.

(Continued)

*Primary Examiner*—Young J Kim
*Assistant Examiner*—Samuel Woolwine
(74) *Attorney, Agent, or Firm*—Harness, Dickey & Pierce, P.L.C.

(57) ABSTRACT

A method of generating a single-stranded nucleic acid molecule comprising (a) combining in a mixture under conditions suitable for a polymerase extension reaction, (i) a polymerase, (ii) an initial polynucleotide comprising a 5' portion and a 3' portion, wherein the polynucleotide forms the nucleic acid molecule 5' end; and (iii) a plurality of overlapping template oligonucleotides each having a 5' template portion and a 3' portion. The method further comprises (b) hybridizing the initial polynucleotide or the extension polynucleotide and one of the template oligonucleotides; (c) incubating the mixture for sufficient time to allow an extension polynucleotide to be synthesized; (d) adding a competimer that competes with the template oligonucleotide in step (b); (e) denaturing the extension polynucleotide and template oligonucleotide; and (f) repeating steps (b), (c), (d), and (e) to generate the single-stranded nucleic acid molecule, wherein the number of repeated cycles equals the number of different template oligonucleotides.

54 Claims, 2 Drawing Sheets

OTHER PUBLICATIONS

Metzker, M. et al.; Termination of DNA Synthesis by Novel 3'-Modified-Deoxyribonucleoside 5'-Triphosphates; Nucleic Acids Research; vol. 22, No. 20, pp. 4259-4267; 1994.

Nasidze, I. et al.; Construction of larger-size sequencing template from degraded DNA; Biotechniques; 27:480-484; 1999.

Pan, W. et al.; Vaccine candidate MSP-1 from *Plasmodium falciparum*: a redesigned 4917 bp polynucleotide enables synthesis and isolation of full-length protein from *Escherichia coli* and mammalian cells; Nucleic Acids Research; vol. 27, No. 4; pp. 1094-1103; 1999.

Sanger, F. et al.; A rapid method for determining sequences in DNA by primed synthesis with DNA polymerase; Journal of Molecular Biology; 94(3): 441-448; 1975.

Sanger, F. et al.; DNA sequencing with chain-terminating inhibitors; Porc. Natl. Acad. Sci. USA; vol. 74, No. 12; pp. 5463-5467; Dec. 1977.

Shevchuk, N.A. et al.; Construction of long DNA molecules using long PCR-based fusion of several fragments simultaneously; Nucleic Acids Research; vol. 32, No. 2; 2004.

Smith et al.; Approach to Genotyping Errors Caused by Nontemplated Nucleotide Addition by Taq DNA merase; Genome Research; vol. 5, No. 3; pp. 312-317; Oct. 1995.

Syvanen, AC et al.; A primer-guided nucleotide incorporation assay in the genotyping apolipoprotein E.; Genomics; pp. 684-692; Dec. 1999.

Translation of JP 09149789 A (1997): Method for Solid Phase Synthesis of Polynucleotides.

Warrens, AN et al.; Splicing by overlap extension by PCR using asymmetric amplification; an improved technique for the generation of hybrid proteins of immunological interest; Gene 186:29-35.

Xiong, A. et al.; A simple, rapid, high-fidelity and cost-effective PCR-based two-step DNA synthesis method for long gene sequences; Nucleic Acids Research; vol. 32, No. 12; Jul. 7, 2004.

Yuzhakov, A.A. et al., 3'-Mercapto-2', 3'-Dideoxynucleotides are High Effective Terminators of DNA Synthesis Catalyzed by HIV Reverse Transcriptase; FEBS Lett.; vol. 306, No. 2,3, pp. 185-188; 1992.

Zheng, Xiaofeng et al.; Efficient construction of long DNA duplexes with internal non-Watson-Crick motifs and modifications; Nucleic Acids Research; vol. 29, No. 2; 2001.

* cited by examiner a) 5'-TGTAAAACGACGGCCAGTAGCCT-3' (SEQ ID NO:1)
3'-ACATTTTGCTGCCGGTCATCGGACTTAACTATTTGAC<u>TTTGACGTGTGAGTGTAT</u>-5' (SEQ ID NO:2)

b) 5'-TGTAAAACGACGGCCAGTAGCCTGAATTGATAAACTGAAACTGCACACTCACATA (SEQ ID NO:3)
3'-<u>TTTGACGTGTGAGTGTAT</u>TAATAGACGTATAA<u>TAGATGGTTAAGACAATT</u>-5' (SEQ ID NO:4)

c) 5'-TGTAAAACGACGGCCAGTAGCCTGAATTGATAAACTGAAACTGCACACTCACATAATT
ATCTGCATATTATCTACCAATTCTGTTAA-3' (SEQ ID NO:5)
3'-ACATTTTGCTGCCGGTCATCGGACTTAACTATTTGAC<u>TTTGACGTGTGAGTGTAT</u>TAA
TAGACGTATAA<u>TAGATGGTTAAGACAATT</u>-5' (SEQ ID NO:6)

d) 5'-TGTAAAACGACGGCCAGTA[---]TATCTGCATATTATCTACCAATTCTGTTAA-3' (SEQ ID NO:5)
3'-<u>TAGATGGTTAAGACAATT</u>TTGGGAAGTGATAGACGTAGATTGGAGGATAA-5' (SEQ ID NO:7)

e) 5'-TGTAAAACGACGGCCAGTA[---]TATCTGCATATTATCTACCAATTCTGTTAAAACCC
TTCACTATCTGCATCTAACCTCCTATT-3' (SEQ ID NO:8)
3'-ACATTTTGCTGCCGGTCAT[---]ATAGACGTATAA<u>TAGATGGTTAAGACAATT</u>TTG
GGAAGTGATAGACGTAGATTGGAGGATAA-5' (SEQ ID NO:9)

FIGURE 1 a) 5'-TGTAAAACGACGGCCAGT-3' (SEQ ID NO:27)
   3'amino-ACATTTTGCTGCCGGTCACTTAACTATTTGAC<u>TTTGACGTGTGAGTGTAT</u>-5' (SEQ ID NO:28)

b) 5'-TGTAAAACGACGGCCAGTGAATTGATAAACTGAAACTGCACACTCACATA-3' (SEQ ID NO:29)
   3'amino-ACATTTTGCTGCCGGTCACTTAACTATTTGAC<u>TTTGACGTGTGAGTGTAT</u>-5' (SEQ ID NO:28)

c) 5'-TGTAAAACGACGGCCAGTGAATTGATAAACTGAAACTGCACACTCACATA-3' (SEQ ID NO:29)
   3'amino-<u>TTTGACGTGTGAGTGTAT</u>TAATAGACGTATAA<u>TAGATGGTTAAGACAATT</u>-5' (SEQ ID NO:30)

d) 5'-TGTAAAACGACGGCCAGTGAATTGATAAACTGAAACTGCACACTCACATAATTATCTGC
   ATATTATCTACCAATTCTGTTAA-3' (SEQ ID NO:31)
   3'amino-<u>TTTGACGTGTGAGTGTAT</u>TAATAGACGTATAA<u>TAGATGGTTAAGACAATT</u>-5' (SEQ ID NO:30)

FIGURE 2

METHOD OF GENERATING LONG NUCLEIC ACID MOLECULES OF DEFINED SEQUENCE

CROSS-REFERENCE TO RELATED APPLICATIONS

This application is a continuation of U.S. patent application Ser. No. 10/819,656, filed on Apr. 7, 2004, which claims the benefit of U.S. Provisional Application No. 60/462,282, filed on Apr. 11, 2003, which are hereby incorporated in their entirety by reference.

FIELD

The present invention relates to nucleic acid synthesis and, in particular, to methods and compositions for the synthesis of long nucleic acid molecules having a defined sequence.

BACKGROUND

Synthesis of oligonucleotides using chemical methods is generally limited to oligonucleotides of a maximum length of about 70 nucleotides to about 100 nucleotides. The synthesis of nucleic acid molecules of longer lengths has required different strategies. For example, one group described the synthesis of a 4917 bp polynucleotide encoding the MSP-1 protein complex of the Plasmodium falciparum malaria parasite (Pan et al., Nucleic Acid Res. 27:1094-1103, 1999). This group used an asymmetric PCR-based synthesis of 600-1100 bp fragments which were then combined via their compatible unique cleavage sites at the ends of successive fragments. The synthesis of the 600-1100 bp fragments was performed using eight oligonucleotides which overlapped with their respective neighboring sequences. Four successive PCR steps were performed. In the first step, adjacent neighboring oligonucleotide pairs were combined in asymmetric proportions to generate four oligonucleotide products which were then combined in pairs with their neighbors to generate two oligonucleotide products. A third PCR step was performed using the first and eighth of the original eight oligonucleotides to reintroduce asymmetry of the two oligonucleotide products. This was then followed by combining the asymmetric products to generate the desired 600-1100 bp fragment. Asymmetric synthesis was performed by using a five to one ratio of the reacting oligonucleotides in order to favor synthesis along one strand during the first and third PCR steps to facilitate synthesis of the final double-stranded product. A similar approach was reported by Cello et al. (Cello et al, Science 297:1016-1018, 2002). These earlier approaches did not suggest any other approach to achieve an asymmetric synthesis along one strand, nor did they suggest a method for synthesis of a single-stranded product.

SUMMARY

Accordingly, the inventors herein have succeeded in discovering methods for synthesizing long, single-stranded nucleic acid molecules of defined sequence using a polymerase extension reaction. The method involves elongation of an initial polynucleotide along a template oligonucleotide which has a 3' portion complementary to a 3' portion of the initial polynucleotide. The template oligonucleotide can comprise a 3'-terminal blocker to prevent extension of the template. Elongation of the initial polynucleotide along the template oligonucleotide produces an extension polynucleotide product. Successive polymerase extension reactions involving the combining of successive template oligonucleotides which have 3' portions complementary with the 3' portions of extension polynucleotide products, results in generation of a long nucleic acid molecule.

Thus, in various configurations, the present invention can provide a method for generating a long single-stranded nucleic acid molecule. The method comprises contacting in a mixture, (i) an initial polynucleotide comprising a 5' portion and a 3' portion; (ii) a template oligonucleotide having a 3' blocker, a 5' template portion, and a 3' portion which is sufficiently complementary to the 3' portion of the initial polynucleotide to hybridize thereto; and (iii) a polymerase. The mixture is exposed to conditions under which the 3' portion of the polynucleotide hybridizes to the 3' portion of the template oligonucleotide and the polymerase elongates the initial polynucleotide to produce an extension polynucleotide product. The 3' blocker on the template oligonucleotide prevents elongation of the template. The mixture is incubated for sufficient time to allow an extension polynucleotide (comprising the initial polynucleotide and nucleotides added by enzymatic addition to its 3' end) to be synthesized. The mixture is then subjected to denaturing conditions to separate the extension polynucleotide and the template oligonucleotide. The method can, thereafter, be repeated in the presence of a second or subsequent template oligonucleotide having a 3' blocker, a 5' template portion, and a 3' portion which is sufficiently complementary to the 3' portion of the previously synthesized extension polynucleotide product to hybridize thereto. The polymerase further elongates the extension polynucleotide product. The method can be repeated as desired to produce a nucleic acid molecule of any desired length. In certain embodiments, the nucleic acid produced can be at least about 100 nucleotides in length, at least about 500 bases in length, or at least about 800 bases in length.

In some configurations, the mixture can further comprise a "competimer," which is an oligonucleotide containing a blocker and a partial sequence of a template oligonucleotide. The sequence of the competimer does not include a 5' portion of the sequence of a template oligonucleotide that has been used as a template for polynucleotide extension. The presence of the competimer in the mixture is expected to compete with a template oligonucleotide for hybridization that has been used as a synthesis template but not compete with a subsequent template oligonucleotide for hybridization to a previously synthesized strand wherein the 3' portion of an extension polynucleotide is complementary to the 3' portion of the subsequent template oligonucleotide.

In some configurations, most template oligonucleotides comprise a 3' blocker, and at least one template oligonucleotide can be non-blocked. In these configurations, some amplification by PCR can be expected.

In certain configurations, the method can comprise contacting in a mixture, (i) an initial polynucleotide comprising a 5' portion and a 3' portion; (ii) a template oligonucleotide having a 5' template portion, and a 3' portion which is sufficiently complementary to the 3' portion of the initial polynucleotide to hybridize thereto; and (iii) a polymerase. The mixture is exposed to conditions in which the 3' portion of the polynucleotide hybridizes to the 3' portion of the first template oligonucleotide and the polymerase elongates the polynucleotide to produce an extension polynucleotide product. In addition, the polymerase elongates the template oligonucleotide to produce an elongated template oligonucleotide. The mixture is then subjected to denaturing conditions to separate the extension polynucleotide product and the elongated template oligonucleotide. The method can thereafter be repeated in the presence of a second or subsequent template oligonucleotide having a 5' template portion, and a 3' portion which is sufficiently complementary to the 3' portion of the previously synthesized elongated polynucleotide product to hybridize thereto. In certain embodiments, the sequence of the 5' template portion of each oligonucleotide overlaps the sequence of the 3' portion of the subsequent template oligonucleotide. The polymerase then further elongates the extension polynucleotide product as well as the template oligonucleotide. The method can be repeated as desired to produce a nucleic acid molecule of any desired length. In various embodiments, the initial polynucleotide and each of the one or more overlapping oligonucleotides consists of not more than 100 nucleotides. In some configurations, one or more template oligonucleotides also comprise a 3' blocker.

In various embodiments, it can be advantageous to promote the hybridization of a second or subsequent template oligonucleotide to an extension polynucleotide in preference to the binding of a previously used template oligonucleotide to the extension polynucleotide when the template oligonucleotides share an overlapping sequence and thereby compete for hybridization to the extension polynucleotide. To promote binding of a second or subsequent template oligonucleotide in preference to a previously used template oligonucleotide, in some configurations the concentration of the second or subsequent template oligonucleotide is increased in comparison to the concentration of the previously used template oligonucleotide.

In some configurations, the sequences of a template oligonucleotide can be selected such that its melting temperature (Tm) is relatively lower than the Tm of a long double stranded DNA as produced using a polymerase chain reaction. When such template oligonucleotides are used, thermal denaturation can be achieved at a temperature less than a denaturation temperature used during a standard polymerase chain reaction, for example 95° C. Use of a lower denaturation temperature will increase the half-life of a polymerase used in a polymerase extension reaction.

In various embodiments, the number of cycles equals the number of different template oligonucleotides. The number of cycles can be, for example, at least 10 cycles or at least 20 cycles. In certain embodiments, the long nucleic acid produced can be at least 200 nucleotides in length, at least 500 bases in length, or at least 800 bases in length. In various embodiments, a blocked template oligonucleotide can be self-overlapping oligonucleotide which comprises a 5' portion and a 3' portion which overlap. Because the 3' portion of an extension polynucleotide synthesized using of a self-overlapping oligonucleotide as template can subsequently bind the 3' portion of the same self-overlapping oligonucleotide, a long polynucleotide can be generated by repeated cycles of hybridization, extension and denaturation.

In certain embodiments, a nucleic acid can be attached to a solid phase support. The solid support can be, for example, a polymer matrix or a controlled-pore glass. The nucleic acid attached to a support can be, for example, an initial oligonucleotide, a template oligonucleotide, an extension polynucleotide, or a long nucleic acid molecule. In certain configurations, the nucleic acid attached to a support can be an initial oligonucleotide. The method of attachment of a nucleic acid can be any method well known to a skilled artisan. In certain configurations, the attachment is a covalent attachment of a nucleic acid to a solid phase support. For example, the 5' end or the 3' of a nucleic acid can be attached to a solid phase support. The attachment can be, for example, through a linker moiety. The linker moiety can be, for example, a phosphate linker, for example a phosphoramidite such as Phosphalink® (Applied Biosystems, Inc.) which can incorporate a phosphate group at either the 5' or the 3' end of a nucleic acid, or an amine linker, for example, a phosphoramidite such as TFA Aminolink™ phosphoramidite (Applied Biosystems, Inc.) which establishes an amino group at the 5'-end of an oligonucleotide during nucleic acid synthesis.

In certain embodiments, a nucleic acid produced using a method disclosed herein can be single-stranded or double-stranded. The long nucleic acid produced can be further propagated in a cloning vector using methods well-known in the art. In certain embodiments, the amount of a long nucleic acid can be amplified by methods well known in the art. In certain configurations, the polymerase reaction is used for amplification of the long nucleic acid.

BRIEF DESCRIPTION OF THE DRAWINGS

FIG. 1 illustrates the sequence of steps involved in the synthesis of a long nucleic acid using a polymerase extension reaction scheme, wherein the template oligonucleotides do not include a blocker.

FIG. 2 illustrates the sequence of steps involved in the synthesis of a long nucleic acid using a polymerase extension reaction scheme, wherein the template oligonucleotides include a blocker.

DETAILED DESCRIPTION OF THE EMBODIMENTS

Unless otherwise indicated, molecular biology methods known in the art are used (see Sambrook, J., et al., Molecular Cloning: A Laboratory Manual; Cold Spring Harbor Laboratory: Plainview, N.Y., 1989) The following definitions are used in describing the various embodiments disclosed herein.

The terms "blocker" or "3' blocker" as used herein refers to a nucleotide or nucleotide analog component, situated at a 3' terminal of an oligonucleotide or polynucleotide, which inhibits enzymatic addition of a subsequent nucleotide or nucleotide analog to the 3' terminal by a polymerase. Non-limiting examples of blockers are disclosed in Sanger et al., Proc. Natl. Acad. Sci. USA 76: 5463-5467, 1977); Hobbs et al., U.S. Pat. No. 5,047,519; Martinez et al., Nucleic Acid Research 27: 1271-1274, 1999; Metzger et al., Nucleic Acid Research 22: 4259-4267, 1994; Yuzhakov et al., FEBS Lett. 306:185-188, 1992; Dyatkina et al., FEBS Lett. 219:151-155, 1987; Chidgeavadze et al., Biochim. Biophys. Acta 868: 145-152, 1986; Chidgeavadze et al.; FEBS Lett. 183: 275-278, 1985; and Chidgeavadze et al., Nucleic Acids Research 12: 1671-1686, 1984). Non-limiting examples of a blocker are a 3'-nucleotide wherein the sugar can be a pentose (for example, a ribose or a deoxyribose) substituted at the 3' carbon, wherein the 3' substituent can be a hydrogen, an amino, an alkylamino, a halogen, a mercaptan, an alkoxy, or an aryloxy.

The term "competimer" as used herein refers to an oligonucleotide comprising a 3' blocker, and in which the sequence of the oligonucleotide is substantially similar or identical to that of a template oligonucleotide except that the 5' portion of the template oligonucleotide is not included.

The term "cycle" as used herein refers to hybridization complex comprising an initial polynucleotide or an extension polynucleotide and a template oligonucleotide, elongation of the initial or extension polynucleotide, and denaturation of the complex. In certain aspects, conditions for hybridization and elongation can be identical.

The term "denaturation" as used herein refers to separation of the strands of a fully or partially double-stranded nucleic acid. A denaturation of a double-stranded nucleic acid can be effected by any means known in the art, such as (but not limited to) heating the double-stranded nucleic acid.

The term "extension polynucleotide" as used herein refers to a polynucleotide to which bases have been added to the 3' end as a result of a polymerase extension reaction.

The term "hybridization" as used herein refers to formation of a double stranded nucleic acid comprising at least two single-stranded nucleic acids. The double-stranded structure can be completely double-stranded or partially double-stranded.

The term "initial polynucleotide" as used herein refers to the first (or, in some configurations, the only) polynucleotide that is subject to hybridization and elongation during the synthesis of a long nucleic acid molecule.

The term "long nucleic acid molecule" as used herein refers to a nucleic acid molecule of at least 100 nucleotides in length.

The term "melting temperature" (Tm) as used herein refers to the temperature at which 50% of an oligonucleotide and its perfect complement are in duplex.

The term "oligonucleotide" as used herein refers to a polymer comprising that can serve as a template for nucleic acid synthesis catalyzed by a polymerase. In some configurations, a nucleotide subunit of an oligonucleotide can comprise a nucleotide base, for example adenine, thymine, cytosine, guanine, or uracil, or a derivative thereof. In some configurations, a nucleotide subunit of an oligonucleotide can further comprise a sugar, for example a five-carbon sugar such as a ribose, a deoxyribose, or a dideoxyribose, or a derivative thereof. In some configurations, a nucleotide subunit of an oligonucleotide can further comprise a moiety that can link a sugar to another sugar, for example a phosphate or a sulphate.

The term "overlap" as used herein refers to a sequence identity shared by a portion of two or more oligonucleotides. The sequence identity is exact or sufficiently similar for the complement of an oligonucleotide to hybridize to an overlapping oligonucleotide under high stringency conditions.

In various configurations, the present invention provides a method for synthesizing a nucleic acid molecule. The nucleic acid molecule can be a single stranded molecule. The nucleic acid molecule can be of any length. In certain configurations, the nucleic acid molecule can be at least about 200 nucleotides in length, at least about 500 nucleotides in length, or at least about 800 nucleotides in length. The single stranded molecule can be converted to a double stranded molecule and/or propagated in a vector using standard methods well known in the art. The vector can be, for example, a plasmid or a virus. A long polynucleotide sequence can be designed to incorporate restriction sites at predetermined sites, in order to facilitate cloning of the long polynucleotide into a vector.

In certain embodiments, the initial polynucleotide can consist of at least about 18 contiguous nucleotides or at least about 30 contiguous nucleotides. In certain embodiments, the initial polynucleotide can consist of no more than 100 contiguous nucleotides. In certain embodiments, template oligonucleotides comprise overlapping sequences, wherein the overlapping sequences are located in a 5' portion of one oligonucleotide and a 3' portion of a different oligonucleotide. In certain embodiments, the overlapping sequences are identical. In certain configurations, the 3' portion of each template oligonucleotide contains a sequence of at least 8 contiguous nucleotides, at least 15 contiguous nucleotides, or at least 20 contiguous nucleotides that is complementary to a sequence of the same length of the 3' portion of the initial polynucleotide or of a 5' portion of an extension polynucleotide. In certain embodiments, the entire sequence of the initial polynucleotide comprises a sequence that is complementary to a contiguous sequence comprising a 3' portion of a template oligonucleotide. In certain configurations, the 3' portion of each template oligonucleotide can hybridize under high stringency conditions to the 3' portion of the initial polynucleotide or an extension polynucleotide. In certain configurations, the 3' portion of each template oligonucleotide exhibits at least 70%, at least 90%, or 100% sequence identity to the complement of the 3' portion of the initial polynucleotide or an extension polynucleotide, wherein the 3' portion of the initial polynucleotide or an extension polynucleotide can be at least 10 contiguous nucleotides.

In certain embodiments, each template oligonucleotide comprises a 3' blocker, a 5' portion and a 3' portion. Each 5' portion comprises at least about 8 contiguous nucleotides, at least about 15 contiguous nucleotides, or at least about 20 contiguous nucleotides and each 3' portion comprises at least about 8 contiguous nucleotides, at least about 15 contiguous nucleotides, at least about 20 contiguous nucleotides or at least about 25 contiguous nucleotides. In certain embodiments, hybridization conditions are selected which are high stringency hybridization conditions. In certain embodiments, hybridization conditions are selected in which 100% complementarity is required between the 3' portion of a template oligonucleotide and the 3' portion of the polynucleotide for a duplex to form. In addition, in certain embodiments hybridization conditions are selected in which the 3' portion of a template oligonucleotide has sufficient complementary to a 3' portion of a polynucleotide to allow formation of a partial duplex structure which can support elongation, wherein sufficient complementarity is at least about 70% complementarity, at least about 80% complementarity, or at least about 90% complementarity. Such conditions are well known to the skilled artisan.

In some embodiments, a mixture for hybridization and extension comprises at least one "competimer" in addition to a polynucleotide and one or more template oligonucleotides. The presence of a competimer is expected to compete for binding of an extension polynucleotide by a template oligonucleotide to a previously synthesized sequence in a hybridization that occurs after the template oligonucleotide has served as a template. For example, if a template oligonucleotide of the sequence AAAAAAAAAGTCAGT-CAAAAAAAA (SEQ ID NO.:30) is used as template to add extend a polynucleotide, yielding a 3' sequence of TTTTTTTTCTGACTTTTTTTTT (SEQ ID NO.:31), the presence of a competimer of sequence GTCAG is expected to inhibit hybridization of the template oligonucleotide in a subsequent cycle, while leaving the 3' portion sequence TTTTTTTT available for hybridization to the 3' portion of a template oligonucleotide of sequence AAAAAAAA.

In certain embodiments, one or more template oligonucleotides in a polymerase extension reaction can be non-blocked. A non-blocked oligonucleotide can also be extended, using an initial polynucleotide or an extension polynucleotide as template. Because an extended template oligonucleotide can further act as a synthesis template, its presence provides for some sequence amplification of an extension polynucleotide by the polymerase chain reaction. In certain aspects, when one or more template oligonucleotides are not blocked but other template oligonucleotides are blocked, the molar ratio of template oligonucleotides can be adjusted to improve yield of long polynucleotide. For example, the molar concentration of blocked template oligonucleotides which hybridize after an non-blocked template oligonucleotide can be about twice that of a non-blocked template oligonucleotide.

In certain aspects, when a single-stranded nucleic acid is synthesized without the use of a template comprising a 3' blocker, the initial polynucleotide comprises at least 20 contiguous nucleotides, and one or more non-blocked template oligonucleotides comprise at least 20 contiguous nucleotides. In certain aspects, when a single-stranded nucleic acid is synthesized without the use of a template comprising a 3' blocker, the initial polynucleotide and each of the one or more overlapping template oligonucleotides consist of not more than 100 contiguous nucleotides. In certain aspects, when a single-stranded nucleic acid is synthesized without the use of a template comprising a 3' blocker, the 3' portion of each template oligonucleotide contains a sequence of at least 8, at least 15, or at least 25 contiguous nucleotides which are complementary to a sequence of the same length of the 3' portion of the initial polynucleotide or of a 3' portion of an extension polynucleotide. In certain aspects, when a single-stranded nucleic acid is synthesized without the use of a template comprising a 3' blocker, the hybridization and denaturation can be repeated any number of times. In some aspects, the number of cycles equals the number of different template oligonucleotides. The number of cycles can be, for example, at least 10 cycles or at least 20 cycles. In addition, in certain aspects, the nucleic acid molecule can contain at least about 200 bases or at least about 500 bases. In certain configurations, when the initial polynucleotide and each of the one or more overlapping template oligonucleotides consist of not more than 100 contiguous nucleotides, at least one of the one or more overlapping template oligonucleotides can comprise a 3' blocker. The blocker can be, for example, a 3', amino-substituted nucleotide or a dideoxy nucleotide. In certain configurations, when a single-stranded nucleic acid is synthesized, one or more template oligonucleotides comprise one oligonucleotide. In such cases, the one oligonucleotide has a sequence of at least about 8 contiguous nucleotides in the 3' portion of the oligonucleotide, which is identical to a sequence of the same length in the 5' portion of the oligonucleotide.

In certain embodiments of the invention, the method comprises first contacting in a mixture, an initial polynucleotide comprising a 5' portion and a 3' portion; a first (or only) template oligonucleotide having a 3' blocker, a 5' template portion, and a 3' portion which is sufficiently complementary to the 3' portion of the polynucleotide to hybridize thereto; and a polymerase. The contacting occurs under conditions in which the 3' portion of the polynucleotide hybridizes to the 3' portion of the template oligonucleotide and the polynucleotide is elongated to produce an elongated polynucleotide product. During the hybridization, the polynucleotide forms a duplex with a first template oligonucleotide, and elongation of the polynucleotide occurs in which nucleotides complementary to the 5' portion of the initial template oligonucleotide are added to the 3' end of the polynucleotide. A new 3' portion of the polynucleotide is thereby created. The first hybridization is followed by a first denaturation. Each cycle thereafter comprises an additional hybridization and an additional denaturation. In each additional hybridization, a second or subsequent template oligonucleotide has a 3' blocker, a 5' template portion, and a 3' portion which is sufficiently complementary to the 3' portion of the first or a subsequent elongated polynucleotide product to hybridize thereto. During the cycles of hybridization and denaturation, the first or subsequent elongated polynucleotide product is elongated to produce the nucleic acid molecule. In some configurations, the 3' portion of the template oligonucleotide contains a sequence of at least 8, at least 15, at least 25, or at least 25 contiguous nucleotides which are complementary to a sequence of the same length of the 3' portion of the polynucleotide or an extension polynucleotide. In some configurations, the entire sequence of the initial polynucleotide is complementary to the sequence of the first (or only) template oligonucleotide. In certain configurations, when the entire sequence of the initial polynucleotide is complementary to the sequence of the first (or only) template, the 5' nucleotide of the initial polynucleotide can form a base pair with the 3' nucleotide of the first template oligonucleotide.

In various embodiments, it can be advantageous to promote the hybridization of a second or subsequent template oligonucleotide to an extension polynucleotide in preference to the binding of a previously used template oligonucleotide to the extension polynucleotide when the template oligonucleotides share an overlapping sequence and thereby compete for hybridization to the extension polynucleotide. To promote binding of a second or subsequent template oligonucleotide in preference to a previously used template oligonucleotide, in some configurations the concentration of the second or subsequent template oligonucleotide is increased in comparison to the concentration of the previously used template oligonucleotide. For example, the molar ratio of the second template oligonucleotide to first template oligonucleotide to initial (or extension) polynucleotide can be 2:1:1, 2:1.2:1, 2:1.5:1, 4:1.5:1, 6:1.5:1, 10:1.5:1, 4:2:1, or 10:2:1.

In some configurations, the sequences of a template oligonucleotide can be selected such that its melting temperature (Tm) is relatively lower than the Tm of a long double stranded DNA as produced using a polymerase chain reaction. When such template oligonucleotides are used, thermal denaturation can be achieved at a temperature less than a denaturation temperature typically used during a polymerase chain reaction, for example 95° C. For example, the oligonucleotide AAAAAAAAAGTCAGTCAAAAAAAA (SEQ ID NO.:30) has a predicted Tm of 63° C., the oligonucleotide AAAAAAAAAGTCAGTCAGTCAAAAAAAA (SEQ ID NO.:31) has a predicted Tm of 68.1° C., and the oligonucleotide AAAAAAAAAGTCAGTCAGTCAGT-CAAAAAAAA (SEQ ID NO.:32) has a predicted Tm of 72° C. under conditions of $[Mg^{+2}]$=25 mM and $[Na^+]$=150 mM [oligonucleotide]=0.1 µM. When these oligonucleotides are used as template oligonucleotides, denaturation during cycling can be thermal denaturation at a temperature less than 95° C., for example 75° C., 80° C., or 85° C.

It will be understood that the method of generating a nucleic acid of predetermined sequence can be considered complete at any point in a cycle. In non-limiting example, the method can be considered complete at the end of a hybridization. There is no limit to the number of cycles that can be used. In some configurations, the number of cycles is at least equal to the number of different template oligonucleotides. In some configurations, a full length single-stranded nucleic acid is synthesized by 10 cycles of hybridization and denaturation, or by 20 cycles of hybridization and denaturation. In various related configurations, when a long nucleic acid molecule is synthesized using a template oligonucleotides wherein each template oligonucleotide comprises a blocker, the nucleic acid molecule can be of any length. In some configurations, the nucleic acid molecule contains at least 200, at least 500, or at least 800 bases. In various related configurations, the initial polynucleotide comprises at least about 18 contiguous nucleotides. In various configurations, the first or subsequent template oligonucleotide comprises at least 20 contiguous nucleotides, and the polynucleotide comprises not more than 100 continuous nucleotides. In various configurations, the 3' portion of a first template oligonucleotide contains a sequence of at least 8 contiguous nucleotides which are complementary to a sequence of the same length of the 3' portion of the polynucleotide or an extension polynucleotide.

In some configurations of the invention, the second and subsequent template oligonucleotides are identical. In such configurations, the 3' portion of each second template oligonucleotide comprises a sequence which is identical to a 5' portion sequence of the same oligonucleotide such that elongation of the first or subsequent polynucleotide elongation product takes place along the 5' template portion of the template oligonucleotides to produce second or subsequent polynucleotide elongation product having a 3' portion which comprises a sequence complementary to the 3' portions of the second template oligonucleotides. The identical 3' and 5' portions of the second template oligonucleotide can comprise at least about 8, at least about 15, or at least about 25 nucleotides. For example, if a template oligonucleotide has a 5' portion sequence identical to its 3' portion sequence, such as AAAAAAAAAGTCAGTCAAAAAAAA (SEQ ID NO.:30), wherein the sequences of the 3' portion and the 5' portion are both AAAAAAAA, the sequence GACTGACTTTTTTTTT (SEQ ID NO.:40) is expected to be added to the 3' terminal of an extension oligonucleotide during each cycle, because the sequence TTTTTTTT is expected to hybridize to the template oligonucleate during each cycle.

In configurations wherein the 3' carbon of the 3'-terminal nucleotide comprises a blocker. Thus, instead of a hydroxy radical, the 3' carbon of a blocker can have as a substituent group, in non-limiting example, a hydrogen, (whereby the sugar moiety of the 3'-terminal nucleotide is either a 3' deoxyribose or a 2', 3' dideoxyribose), an alkyl moiety, an alkoxy moiety, an amine, an ester, an alkylamine, a halogen, a sulfide, or a sulfate. In certain configurations, the 3' carbon of a blocker can have as a substituent a hydrogen or an amino group.

In various embodiments of the invention, the polymerase is a primer-dependent and template-dependent polymerase and can be a DNA polymerase, a DNA-dependent RNA polymerase, a reverse transcriptase, or an RNA-dependent RNA polymerase. In certain configurations, the polymerase can be a thermal stable polymerase. In certain configurations, the thermal stable polymerase can be a Taq polymerase or a Tth polymerase. A DNA polymerase can also be an *E. coli* DNA polymerase such as a DNA pol I polymerase, or a Klenow fragment thereof.

The conditions in which the 3' portion of the polynucleotide hybridizes to the 3' portion of the template oligonucleotide and elongates to produce an extension polynucleotide product are non-denaturing conditions that allow both hybridization and elongation of the hybridized polynucleotide to occur. Such conditions are well known to a skilled artisan.

In certain aspects, the long nucleic acid molecule is a DNA molecule. In these aspects, the polymerase is a DNA polymerase, and the nucleoside triphosphate precursor molecules are deoxyribonucleoside triphosphate molecules (dNTP's). In certain other aspects, the long nucleic acid molecule is an RNA molecule. In these aspects, the polymerase is an RNA polymerase, and the nucleoside triphosphate precursor molecules are ribonucleoside triphosphate molecules (NTP's).

The conditions in which the 3' portion of the initial polynucleotide hybridizes to the 3' portion of the template oligonucleotide and elongates to produce an elongated polynucleotide product are non-denaturing conditions that allow both hybridization and elongation of the hybridized polynucleotide to occur. Such conditions are well known to a skilled artisan. The hybridization conditions allow a partial duplex to form between the polynucleotide and a template oligonucleotide, whereby the 5' portion can serve as a template for an elongation reaction catalyzed by the polymerase. The hybridization conditions in a mixture that allows partial duplex formation comprise buffer conditions, salt conditions, and temperature conditions such as those described in Sambrook, J., et al., Molecular Cloning: A Laboratory Manual; Cold Spring Harbor Laboratory: Plainview, N.Y., 1989. Furthermore, hybridization conditions also comprise buffer, salt, and temperature conditions that allow a polymerase to catalyze an elongation reaction when a primer and template are provided. These conditions comprise inclusion in the mixture of one or more nucleoside triphosphate precursor molecules. In certain embodiments, hybridization conditions are selected in which an initial or extension polynucleotide and a template oligonucleotide are sufficiently complementary to hybridize. For example, the length and the percentage complementarity of a polynucleotide and an templateoligonucleotide can be selected to be sufficiently complementary to hybridize. In some configurations, 100% complementarity is required between the 3' portion of the polynucleotide and the 3' portion of a template oligonucleotide for a partial duplex to form which can support elongation. In certain other embodiments, hybridization conditions are selected to be high stringency conditions in which sufficient complementarity between the 3' portion of the polynucleotide and the 3' portion of a template oligonucleotide is required for a partial duplex to form which can support elongation, wherein sufficient complementarity is at least about 70% complementarity, at least 80% complementarity, or at least 90% complementarity.

Denaturing conditions in various embodiments of the invention are conditions well known to skilled artisans. In various embodiments, denaturation conditions comprise heating a mixture comprising a fully or partially double-stranded nucleic acid to at least 75° C., at least 80° C., or at least 90° C. It will be understood that the denaturation conditions can be selected to be reversible, that is, conditions can be changed allowing for further hybridization of a polynucleotide. The duration of the denaturing is determined using methods well known to skilled artisans. In some embodiments, when the denaturing utilizes a high temperature (for example, 90° C.) to separate strands in a mixture, the mixture can be held at the high temperature for a duration of, for example, 20 sec., 40 sec., 60 sec., or 90 sec. However, in certain embodiments, little or no amplification of the long polynucleotide is expected to occur. Accordingly, in these embodiments, the amount of initial polynucleotide and template oligonucleotide in a mixture can be greater than the amount of primers used in standard PCR reactions (Sambrook et al., Molecular Cloning: A Laboratory Manual; Cold Spring Harbor Laboratory: Plainview, N.Y. (1989)), and the extension time for each cycle can be greater than that of standard PCR reactions, for example at least 3 min., at least 4 min., or at least 5 min.

In certain aspects, some template oligonucleotides in a mixture do not comprise a 3' blocker. Instead, the 3' nucleotide of these oligonucleotides comprise a moiety which can serve as a substrate for elongation by a polymerase, for example a standard ribose or deoxyribose sugar moiety. The presence of these template oligonucleotides provide for some sequence amplification of the polynucleotide and its complement by the polymerase chain reaction. Because it is possible that loss of reaction products will occur during cycles of hybridization and denaturation, an elongatable template oligonucleotide can be included in a mixture. Its inclusion leads to amplification of a polynucleotide (and its complementary strand) by the polymerase chain reaction. The extension polynucleotide product of an amplification reaction can serve as a substrate for elongation during a subsequent hybridization. In certain embodiments, the final template oligonucleotide can be a primer for a polymerase chain reaction, and can be used to amplify the final long polynucleotide product.

In various embodiments, the present invention provides a method for generating a long single-stranded nucleic acid molecule. The method comprises contacting in a mixture, (i) a polynucleotide comprising a 5' portion and a 3' portion; (ii) a template oligonucleotide having a 3' blocker, a 5' template portion, and a 3' portion which is sufficiently complementary to the 3' portion of the polynucleotide to hybridize thereto; and (iii) a polymerase. The mixture is exposed to conditions in which the 3' portion of the polynucleotide hybridizes to the 3' portion of the template oligonucleotide and the polymerase elongates the polynucleotide to produce an extension polynucleotide product. The mixture is then subjected to denaturing conditions to separate the extension polynucleotide product and the template oligonucleotide. The method can thereafter be repeated in the presence of a second or subsequent template oligonucleotide having or not having a 3' blocker, a 5' template portion, and a 3' portion which is sufficiently complementary to the 3' portion of the previously synthesized extension polynucleotide product to hybridize thereto. The inclusion of a non-blocked template oligonucleotide in the mixture can lead to formation of a complement of an entire extended polynucleotide. This complement of an extended polynucleotide can serve as template for elongation in subsequent cycles of hybridization and denaturation, and thereby increase the amount of long nucleic acid formed. In some embodiments, every tenth template oligonucleotide (if template oligonucleotides are considered in the order in which they are used as template) can be a non-blocked oligonucleotide. In some embodiments, the final template oligonucleotide used to generate a full-length long nucleic acid can be a non-blocked oligonucleotide, so that increased quantities of full-length long nucleic acid can be generated by the polymerase chain reaction (PCR) using repeated cycles, in which the initial polynucleotide and final (non-blocked) template oligonucleotide act as primers for amplification by PCR.

In some configurations, following synthesis of a long single-stranded polynucleotide in a mixture, the long single-stranded polynucleotide can be isolated from the mixture. The isolating can be by any method known in the art. In certain configurations, the isolating comprises binding the long polynucleotide to a solid phase medium, and eluting the long polynucleotide from the solid phase medium. The solid phase medium can comprise a polymer matrix. The polymer matrix can comprise a template oligonucleotide, for example a template oligonucleotide covalently attached to the polymer. In some configurations, the final template oligonucleotide used as a template for extension of the polynucleotide can be the template oligonucleotide covalently attached to a polymer matrix. In certain configurations, the polymer matrix can comprise a charged matrix, for example a DEAE matrix. Elution can be by any means known in the art. Elution can comprise, for example, altering the pH or ion concentration in the medium contacting the matrix.

When a DNA molecule is synthesized, the polymerase is a DNA polymerase, and the nucleoside triphosphate precursor molecules are deoxyribonucleoside triphosphate molecules (dNTP's). A dNTP can be, for example, deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP). When an RNA molecule is synthesized, the polymerase is an RNA polymerase, and the nucleoside triphosphate precursor molecules are ribonucleoside triphosphate molecules (NTP's). An NTP can be, for example, adenosine triphosphate (ATP), guanosine triphosphate (GTP), cytidine triphosphate (CTP), thymidine triphosphate (TTP) and uridine triphosphate (UTP). In addition, various modified dNTP and NTP can be used in the synthesis of a long oligonucleotide. In non-limiting example, a modified dNTP or NTP can comprise a label, for example a fluorophore such as VIC®, FAM®, ROX®, LIZ® or TAMRA® (Applied Biosytems, Inc.), a chromophore, a biotin, a hapten (for example bromodeoxyuridine or digoxygenin) or a chemiluminescent moiety, a radioisotope (for example, a $^3$H, a $^{14}$C, a $^{32}$P, or a $^{33}$P), or a spin label.

In various embodiments, a DNA polymerase is any DNA polymerase which can catalyze a primer-dependent and template-dependent polynucleotide extension in vitro. Non-limiting examples of a DNA polymerase include a thermostable DNA polymerase such as Taq polymerase or Tth polymerase, or a non-thermostable polymerase such as an *E. coli* DNA polymerase I enzyme or a fragment thereof, such as a Klenow fragment of *E. coli* DNA polymerase I. An RNA polymerase can be any RNA polymerase which can catalyze a primer-dependent and template-dependent polynucleotide extension in vitro. Non-limiting examples of an RNA polymerase include a thermostable RNA polymerase such as a Tth RNA polymerase, and *E. coli* RNA polymerase I, or a viral RNA-dependent RNA polymerase.

The invention will be further understood by reference to the examples which follow.

EXAMPLE 1

This example illustrates synthesis of a long nucleic acid according to an embodiment of the invention in which the template oligonucleotides do not comprise a 3' blocker. FIG. 1 illustrates the sequence of steps involved in the synthesis of a long nucleic acid using a polymerase extension reaction scheme, and shows SEQ ID NO: 1 through SEQ ID NO:9, with overlapping sequences indicated by underscoring, (single underscore, double underscore, or broken underscore marks). As shown in FIG. 1, in order to synthesize a long nucleic acid, a mixture is formed comprising an initial polynucleotide (a 23-mer, SEQ ID NO: 1, as listed in Table 1), a first template oligonucleotide (a 55-mer, SEQ ID NO:2, as listed in Table 1), and a polymerase. The initial polynucleotide and the first template oligonucleotide hybridize (FIG. 1a). In this example, the entire initial polynucleotide is complementary to the template oligonucleotide, with the 3' terminal nucleotide of the template oligonucleotide base-pairing with the 5' terminal nucleotide of the initial polynucleotide. The polymerase catalyzes elongation of the initial polynucleotide, yielding a double-stranded nucleic acid of 55 base pairs. The double-stranded nucleic acid is then denatured, thereby yielding a first extension polynucleotide (a 55-mer, SEQ ID NO:3, as listed in Table 1) as well as releasing the first template oligonucleotide from the complex. The mixture is then returned to non-denaturing conditions, where a new hybridization complex is formed between the first extension polynucleotide and a second template oligonucleotide (a 50-mer, SEQ ID NO: 4, as listed in Table 1) (FIG. 1b). Note that the 3' portion of the second template oligonucleotide (consisting of 18 nucleotides) is identical in sequence to the 5' portion of the first template oligonucleotide, and hence, is complementary to the 3' portion of the first extension polynucleotide. Further extension of the first extension polynucleotide, as well as extension of the second template oligonucleotide, yields a double-stranded nucleic acid of 87 base pairs (FIG. 1c). Denaturation of this double-stranded molecule yields a second extension polynucleotide of 87 bases (SEQ ID NO: 5, as listed in Table 1), as well as an extension template oligonucleotide of 87 bases (SEQ ID NO: 6, as listed in Table 1). A third hybridization then forms between the second extension oligonucleotide and a third template oligonucleotide, a 50-mer (SEQ ID NO:7, as listed in Table 1) (FIG. 1d). In this hybridization complex, 18 nucleotides of the 3' end of the extension polynucleotide are complementary to 18 nucleotides of the 3' end of the template oligonucleotide. Extension of the strands of this complex yields a double stranded molecule of 119 base pairs (FIG. 1e). This double stranded molecule can be denatured into 2 single stranded molecules, including a third extension polynucleotide, a 119-mer (SEQ ID NO:8, as listed in Table 1 and its complement (SEQ ID NO:9, as listed in Table 1). In subsequent cycles of hybridization, elongation and denaturation using the remaining template oligonucleotides (SEQ ID NO:10 through SEQ ID NO:25, as listed in Table 1), each template oligonucleotide is a 50-mer, including 18 nucleotides at the 3' portion that are overlapping to 18 nucleotides of the previously hybridized template oligonucleotide. A final extension polynucleotide is a long polynucleotide, a 631-mer (SEQ ID NO:26, as listed in Table 1):

TABLE 1

| | |
|---|---|
| TGTAAAACGACGGCCAGTAGCCT | SEQ ID NO:1 |
| ATGTGAGTGTGCAGTTTCAGTTTATCAATTCAGGCTA CTGGCCGTCGTTTTACA | SEQ ID NO:2 |
| TGTAAAACGACGGCCAGTAGCCTGAATTGATAAACTG AAACTGCACACTCACATA | SEQ ID NO:3 |
| TTAACAGAATTGGTAGATAATATGCAGATAATTATGT GAGTGTGCAGTTT | SEQ ID NO:4 |
| TGTAAAACGACGGCCAGTAGCCTGAATTGATAAACTG AAACTGCACACTCACATAATTATCTGCATATTATCTA CCAATTCTGTTAA | SEQ ID NO:5 |
| TTAACAGAATTGGTAGATAATATGCAGATAATTATGT GAGTGTGCAGTTTCAGTTTATCAATTCAGGCTACTGG CCGTCGTTTTACA | SEQ ID NO:6 |
| AATAGGAGGTTAGATGCAGATAGTGAAGGGTTTTAAC AGAATTGGTAGAT | SEQ ID NO:7 |
| TGTAAAACGACGGCCAGTAGCCTGAATTGATAAACTG AAACTGCACACTCACATAATTATCTGCATATTATCTA CCAATTCTGTTAAAACCCTTCACTATCTGCATCTAAC CTCCTATT | SEQ ID NO:8 |
| AATAGGAGGTTAGATGCAGATAGTGAAGGGTTTTAAC AGAATTGGTAGATAATATGCAGATAATTATGTGAGTG TGCAGTTTCAGTTTATCAATTCAGGCTACTGGCCGTC GTTTTACA | SEQ ID NO:9 |
| AATAAGAACAGATACAGTAAATTATAAGCAGTAATAG GAGGTTAGATGCA | SEQ ID NO:10 |
| CAGATTTAGTTGGAGGTTATCAGTTAGGATATAATAA GAACAGATACAGT | SEQ ID NO:11 |
| GTATGTATGAGACAGATTGGGTGATATAAAGTCAGAT TTAGTTGGAGGTT | SEQ ID NO:12 |
| GAGTCAGTTACAGAATGATGAATGCAGTTATTGTATG TATGAGACAGATT | SEQ ID NO:13 |
| TATTAGCTGAATTGAGCAGTTTTAGGGAGTTTGAGTC AGTTACAGAATGA | SEQ ID NO:14 |
| TTAATGGACAGTATAGTTGGTGTAAGAGCAGTTATTA GCTGAATTGAGCA | SEQ ID NO:15 |

TABLE 1-continued

| | |
|---|---|
| CAGTTTCAGAAATGGAAGAGCAGAAATAGAATTTAAT GGACAGTATAGTT | SEQ ID NO:16 |
| TTGAGGAGGGAACAGTATGATGGGTTGTGTGTCAGTT TCAGAAATGGAAG | SEQ ID NO:17 |
| TAATCAGTTAGGTGAAGAAATTTACAGTTTGTTTGAG GAGGGAACAGTAT | SEQ ID NO:18 |
| AACAGATAAAGAGAGGCAGAATGGGTATGGTTTAATC AGTTAGGTGAAGA | SEQ ID NO:19 |
| GGTAATGGCAGATATAGGGATAGGTAGTCAGTAACAG ATAAAGAGAGGCA | SEQ ID NO:20 |
| CAGAAATTAGAGTTGGAAATCAGAATTTGTTTGGTAA TGGCAGATATAGG | SEQ ID NO:21 |
| GTTTATAGAGTACTGATATGGTTTGGGAAGATCAGAA ATTAGAGTTGGAA | SEQ ID NO:22 |
| TGTACAGTAAGAAAATGGATATTACAGAATCTGTTTA TAGAGTACTGATA | SEQ ID NO:23 |
| AATGTTGTAGAAGGTGCAGATAGATTAAGATTTGTAC AGTAAGAAAATGG | SEQ ID NO:24 |
| GTATGATACAGTTATTAGTGGTTGTTGACAGTAATGT TGTAGAAGGTGCA | SEQ ID NO:25 |
| TGTAAAACGACGGCCAGTAGCCTGAATTGATAAACTG AAACTGCACACTCACATAATTATCTGCATATTATCTA CCAATTCTGTTAAAACCCTTCACTATCTGCATCTAAC CTCCTATTACTGCTTATAATTTACTGTATCTGTTCTT ATTATATCCTAACTGATAACCTCCAACTAAATCTGAC TTTATATCACCCAATCTGTCTCATACATACAATAACT GCATTCATCATTCTGTAACTGACTCAAACTCCCTAAA ACTGCTCAATTCAGCTAATAACTGCTCTTACACCAAC TATACTGTCCATTAAATTCTATTTCTGCTCTTCCATT TCTGAAACTGACACACAACCCATCATACTGTTCCCTC CTCAAACAAACTGTAAATTTCTTCACCTAACTGATTA AACCATACCCATTCTGCCTCTCTTTATCTGTTACTGA CTACCTATCCCTATATCTGCCATTACCAAACAAATTC TGATTTCCAACTCTAATTTCTGATCTTCCCAAACCAT ATCAGTACTCTATAAACAGATTCTGTAATATCCATTT TCTTACTGTACAAATCTTAATCTATCTGCACCTTCTA CAACATTACTGTCAACAACCACTAATAACTGTATCAT AC | SEQ ID NO:26 |

EXAMPLE 2

This example illustrates synthesis of a long nucleic acid according to an embodiment of the invention in which the template oligonucleotides each comprise a 3' blocker. FIG. 2 illustrates the sequence of steps involved in the synthesis of a long nucleic acid using a polymerase extension reaction scheme, and shows SEQ ID NO:27 through SEQ ID NO:31, with overlapping sequences indicated by underscoring as in FIG. 1. As shown in FIG. 2, in order to synthesize a long nucleic acid, a mixture is formed comprising an initial polynucleotide, (an 18-mer, SEQ ID NO: 27 as listed in Table 2), a first template oligonucleotide (a 50-mer, SEQ ID NO: 28 as listed in Table 2) wherein the 3' nucleotide is a blocker; and a polymerase. In this example, the blocker modification is a deoxyribose modified with a 3' amino group. The initial polynucleotide and the first template oligonucleotide hybridize (FIG. 2a). In this example, the entire initial polynucleotide is complementary to the template oligonucleotide, with the 3' terminal nucleotide of the template oligonucleotide base-pairing with the 5' terminal nucleotide of the initial polynucleotide. The polymerase catalyzes elongation of the initial polynucleotide, yielding a double-stranded nucleic acid of 50 base pairs (SEQ ID NO: 28 and SEQ ID NO:29 as listed in table 2) (FIG. 2b). The double-stranded nucleic acid is then denatured, thereby yielding a first extension polynucleotide of 50 bases as well as releasing the first template oligonucleotide from the complex. The mixture is then returned to non-denaturing conditions, where a new hybridization complex is formed between the first extension polynucleotide (SEQ ID NO: 29) and a second template oligonucleotide (a 50-mer, SEQ ID NO: 30) (FIG. 2c). In the hybridization complex, the 3' portion of the first extension polynucleotide consists of 18 nucleotides which are complementary to 18 nucleotides of the 3' portion of the first template oligonucleotide. Elongation of the first extension polynucleotide yields a partially double stranded nucleic acid molecule consisting of the second template oligonucleotide, a 50-mer (SEQ ID NO: 30 as listed in table 2) and a second extension polynucleotide, an 82-mer (SEQ ID NO: 31 as listed in table 2) (FIG. 2d). Denaturation of this partially double stranded molecule releases both the second template oligonucleotide and the second extension polynucleotide from the complex. In subsequent cycles of hybridization, elongation and denaturation using the remaining template oligonucleotides (SEQ ID NO:32-through SEQ ID NO:38, as listed in table 2), each template oligonucleotide is a 50-mer that includes a blocker and 18 nucleotides at the 3' portion that are overlapping to 18 nucleotides of the previously hybridized template oligonucleotide. A final extension polynucleotide is a long polynucleotide, a 306-mer (SEQ ID NO: 39, as listed in table 2).

TABLE 2

TGTAAAACGACGGCCAGT SEQ ID NO:27

TATGTGAGTGTGCAGTTTCAGTTTATCAATTCACTGG SEQ ID NO:28
CCGTCGTTTTACA-amine

TGTAAAACGACGGCCAGTGAATTGATAAACTGAAACT SEQ ID NO:29
GCACACTCACATA

TTAACAGAATTGGTAGATAATATGCAGATAATTATGT SEQ ID NO:30
GAGTGTGCAGTTT-amine

TABLE 2-continued

TGTAAAACGACGGCCAGTGAATTGATAAACTGAAACT SEQ ID NO:31
GCACACTCACATAATTATCTGCATATTATCTACCAAT
TCTGTTAA

AATAGGAGGTTAGATGCAGATAGTGAAGGGTTTTAAC SEQ ID NO:32
AGAATTGGTAGAT-amine

AATAAGAACAGATACAGTAAATTATAAGCAGTAATAG SEQ ID NO:33
GAGGTTAGATGCA-amine

CAGATTTAGTTGGAGGTTATCAGTTAGGATATAATAA SEQ ID NO:34
GAACAGATACAGT-amine

GTATGTATGAGACAGATTGGGTGATATAAAGTCAGAT SEQ ID NO:35
TTAGTTGGAGGTT-amine

GAGTCAGTTACAGAATGATGAATGCAGTTATTGTATG SEQ ID NO:36
TATGAGACAGATT-amine

TATTAGCTGAATTGAGCAGTTTTAGGGAGTTTGAGTC SEQ ID NO:37
AGTTACAGAATGA-amine

TTAATGGACAGTATAGTTGGTGTAAGAGCAGTTATTA SEQ ID NO:38
GCTGAATTGAGCA-amine

TGTAAAACGACGGCCAGTGAATTGATAAACTGAAACT SEQ ID NO:39
GCACACTCACATAATTATCTGCATATTATCTACCAAT
TCTGTTAAAACCCTTCACTATCTGCATCTAACCTCCT
ATTACTGCTTATAATTTACTGTATCTGTTCTTATTAT
ATCCTAACTGATAACCTCCAACTAAATCTGACTTTAT
ATCACCCAATCTGTCTCATACATACAATAACTGCATT
CATCATTCTGTAACTGACTCAAACTCCCTAAAACTGC
TCAATTCAGCTAATAACTGCTCTTACACCAACTATAC
TGTCCATTAA

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:

1. A method of generating a single-stranded nucleic acid molecule, the method comprising:
   (a) combining in a mixture under conditions suitable for a polymerase extension reaction:
      (i) a polymerase,
      (ii) an initial polynucleotide comprising a 5' portion and a 3' portion, wherein the polynucleotide forms the nucleic acid molecule 5' end; and
      (iii) a plurality of overlapping template oligonucleotides each having a 5' template portion and a 3' portion, wherein the 3' portion of each template oligonucleotide is sufficiently complementary to the 3' portion of one of: the initial polynucleotide or a 3' portion of an extension polynucleotide formed by a polymerase extension reaction of the initial polynucleotide,
   (b) hybridizing the initial polynucleotide or the extension polynucleotide and one of the template oligonucleotides;
   (c) incubating the mixture for sufficient time to allow an extension polynucleotide to be synthesized;
   (d) adding a competimer that competes with the template oligonucleotide in step (b);
   (e) denaturing the extension polynucleotide and template oligonucleotide; and
   (f) repeating steps (b), (c), (d), and (e) to generate the single-stranded nucleic acid molecule, wherein the number of repeated cycles equals the number of different template oligonucleotides.

2. The method of generating a single-stranded nucleic acid molecule according to claim 1, wherein the competimer in step (d) is an oligonucleotide containing a 3' blocker and a partial sequence of the template oligonucleotide in step (b).

3. The method of generating a single-stranded nucleic acid molecule according to claim 1, wherein the competimer in step (d) is an oligonucleotide that does not include a 5' portion of the sequence of a the template oligonucleotide in step (b).

4. The method of generating a single-stranded nucleic acid molecule according to claim 1, wherein the competimer in step (d) competes with the template oligonucleotide in step (b) but does not compete with a subsequent template oligonucleotide capable of hybridizing to the 3' portion of the extension polynucleotide synthesized in step (c).

5. The method of generating a single-stranded nucleic acid molecule according to claim 1, wherein the number of repeated cycles in step (f) equals the number of different template oligonucleotides.

6. The method of generating a single-stranded nucleic acid molecule according to claim 1, wherein the initial polynucleotide and each of the plurality of overlapping template oligonucleotides consist of not more than 100 contiguous nucleotides.

7. The method of generating a single-stranded nucleic acid molecule according to claim 1, further comprising isolating the nucleic acid molecule from the mixture.

8. The method of generating a single-stranded nucleic acid molecule according to claim 7, wherein isolating the single-stranded nucleic acid molecule from the mixture is by binding the single-stranded nucleic acid to a column and eluting the single-stranded nucleic acid from the column.

9. The method of generating a single-stranded nucleic acid molecule according to claim 1, wherein the single-stranded nucleic acid molecule contains at least about 200 bases.

10. The method of generating a single-stranded nucleic acid molecule according to claim 1, wherein the single-stranded nucleic acid molecule contains at least about 500 bases.

11. The method of generating a single-stranded nucleic acid molecule according to claim 1, wherein the initial polynucleotide comprises at least 20 contiguous nucleotides.

12. The method of generating a single-stranded nucleic acid molecule according to claim 1, wherein the one or more template oligonucleotides comprises at least 20 contiguous nucleotides.

13. The method of generating a single-stranded nucleic acid molecule according to claim 1, wherein the 3' portion of each template oligonucleotide contains a sequence of at least 8 contiguous nucleotides which are complementary to a sequence of the same length of the 3' portion of the initial polynucleotide or of a 3' portion of an extension polynucleotide.

14. The method of generating a single-stranded nucleic acid molecule according to claim 1, wherein the 3' portion of each template oligonucleotide contains a sequence of at least 15 contiguous nucleotides which are complementary to a sequence of the same length of the 3' portion of the initial polynucleotide or of a 3' portion of an extension polynucleotide.

15. The method of generating a single-stranded nucleic acid molecule according to claim 1, wherein the 3' portion of each template oligonucleotide contains a sequence of at least 25 contiguous nucleotides which are complementary to a sequence of the same length of the 3' portion of the initial polynucleotide or of a 3' portion of an extension polynucleotide.

16. The method of generating a single-stranded nucleic acid molecule according to claim 1, wherein the number of repeated cycles in step (e) equals at least 10 cycles.

17. The method of generating a single-stranded nucleic acid molecule according to claim 1, wherein the number of repeated cycles in step (e) equals at least 20 cycles.

18. The method of generating a single-stranded nucleic acid molecule according to claim 1, wherein at least one of the plurality of overlapping template oligonucleotides comprises a 3' blocker.

19. The method of generating a single-stranded nucleic acid molecule according to claim 18, wherein the 3' blocker is a 3', amino-substituted nucleotide or a dideoxy nucleotide.

20. The method of generating a single-stranded nucleic acid molecule according to claim 1, wherein at least one of the initial oligonucleotide, template oligonucleotide, extension polynucleotide, or the single-stranded nucleic acid molecule is attached to a solid phase support.

21. The method of generating a single-stranded nucleic acid molecule according to claim 20, wherein the initial polynucleotide is attached to the solid support.

22. The method of generating a single-stranded nucleic acid molecule according to claim 20, wherein the solid phase support is selected from a polymer matrix and a controlled-pore glass.

23. The method of generating a single-stranded nucleic acid molecule according to claim 20, wherein the at least one of the initial polynucleotide or template oligonucleotide is attached at a 5' end.

24. The method of generating a single-stranded nucleic acid molecule according to claim 20, wherein the template oligonucleotide is attached at a 3' end.

25. The method of generating a single-stranded nucleic acid molecule according to claim 20, wherein the at least one of the initial oligonucleotide, template oligonucleotide, extension polynucleotide, or single-stranded nucleic acid molecule attached to a solid phase support is attached through a linker moiety.

26. The method of generating a single-stranded nucleic acid molecule according to claim 25, wherein the linker moiety is selected from a phosphate linker and an amine linker.

27. The method of generating a single-stranded nucleic acid molecule according to claim 1, further comprising amplifying the single-stranded nucleic acid molecule by the polymerase chain reaction.

28. A method of generating a single-stranded nucleic acid molecule, the method comprising:
(a) combining in a mixture under conditions suitable for a polymerase extension reaction:
(i) a polymerase,
(ii) an initial polynucleotide comprising a 5' portion and a 3' portion, wherein the polynucleotide forms the nucleic acid molecule 5' end; and
(iii) a plurality of overlapping template oligonucleotides each having a 5' template portion and a 3' portion, wherein the 3' portion of each template oligonucleotide is sufficiently complementary to the 3' portion of one of: the initial polynucleotide or a 3' portion of an extension polynucleotide formed by a polymerase extension reaction of the initial polynucleotide,
wherein, the concentration of each subsequent template oligonucleotide is greater than the concentration of the previous template nucleotide used to form the extension polynucleotide;
(b) hybridizing the initial polynucleotide or the extension polynucleotide and one of the template oligonucleotides;
(c) incubating the mixture for sufficient time to allow an extension polynucleotide to be synthesized;
(d) denaturing to fully separate the extension polynucleotide and template oligonucleotide; and
(e) repeating steps (b), (c), and (d) to generate the single-stranded nucleic acid molecule.

29. The method of generating a single-stranded nucleic acid molecule according to claim 28, wherein the number of repeated cycles in step (e) equals the number of different template oligonucleotides.

30. The method of generating a single-stranded nucleic acid molecule according to claim 28, wherein the molar ratio of each subsequent template oligonucleotide to the previous template nucleotide to the initial polynucleotide or the extension polynucleotide formed by a polymerase extension reaction of the initial polynucleotide is 2:1:1, 2:1.2:1, 2:1.5:1, 4:1.5:1, 6:1.5:1, 10:1.5:1, 4:2:1, or 10:2:1.

31. The method of generating a single-stranded nucleic acid molecule according to claim 28, wherein the initial polynucleotide and each of the plurality of overlapping template oligonucleotides consist of not more than 100 contiguous nucleotides.

32. The method of generating a single-stranded nucleic acid molecule according to claim 28, further comprising isolating the nucleic acid molecule from the mixture.

33. The method of generating a single-stranded nucleic acid molecule according to claim 32, wherein isolating the single-stranded nucleic acid molecule from the mixture is by binding the single-stranded nucleic acid to a column and eluting the single-stranded nucleic acid from the column.

34. The method of generating a single-stranded nucleic acid molecule according to claim 28, wherein the single-stranded nucleic acid molecule contains at least about 200 bases.

35. The method of generating a single-stranded nucleic acid molecule according to claim 28, wherein the single-stranded nucleic acid molecule contains at least about 500 bases.

36. The method of generating a single-stranded nucleic acid molecule according to claim 28, wherein the initial polynucleotide comprises at least 20 contiguous nucleotides.

37. The method of generating a single-stranded nucleic acid molecule according to claim 28, wherein the one or more template oligonucleotides comprises at least 20 contiguous nucleotides.

38. The method of generating a single-stranded nucleic acid molecule according to claim 28, wherein the 3' portion of each template oligonucleotide contains a sequence of at least 8 contiguous nucleotides which are complementary to a sequence of the same length of the 3' portion of the initial polynucleotide or of a 3' portion of an extension polynucleotide.

39. The method of generating a single-stranded nucleic acid molecule according to claim 28, wherein the 3' portion of each template oligonucleotide contains a sequence of at least 15 contiguous nucleotides which are complementary to a sequence of the same length of the 3' portion of the initial polynucleotide or of a 3' portion of an extension polynucleotide.

40. The method of generating a single-stranded nucleic acid molecule according to claim 28, wherein the 3' portion of each template oligonucleotide contains a sequence of at least 25 contiguous nucleotides which are complementary to a sequence of the same length of the 3' portion of the initial polynucleotide or of a 3' portion of an extension polynucleotide.

41. The method of generating a single-stranded nucleic acid molecule according to claim 28, wherein the number of repeated cycles in step (e) equals at least 10 cycles.

42. The method of generating a single-stranded nucleic acid molecule according to claim 28, wherein the number of repeated cycles in step (e) equals at least 20 cycles.

43. The method of generating a single-stranded nucleic acid molecule according to claim 28, wherein at least one of the plurality of overlapping template oligonucleotides comprises a 3' blocker.

44. The method of generating a single-stranded nucleic acid molecule according to claim 43, wherein the 3' blocker is a 3', amino-substituted nucleotide or a dideoxy nucleotide.

45. The method of generating a single-stranded nucleic acid molecule according to claim 28, wherein at least one of the initial oligonucleotide, template oligonucleotide, extension polynucleotide, or the single-stranded nucleic acid molecule is attached to a solid phase support.

46. The method of generating a single-stranded nucleic acid molecule according to claim 45, wherein the initial polynucleotide is attached to the solid support.

47. The method of generating a single-stranded nucleic acid molecule according to claim 45, wherein the solid phase support is selected from a polymer matrix and a controlled-pore glass.

48. The method of generating a single-stranded nucleic acid molecule according to claim 45, wherein the at least one of the initial polynucleotide or template oligonucleotide is attached at a 5' end.

49. The method of generating a single-stranded nucleic acid molecule according to claim 45, wherein the template oligonucleotide is attached at a 3' end.

50. The method of generating a single-stranded nucleic acid molecule according to claim 45, wherein the at least one of the initial oligonucleotide, template oligonucleotide, extension polynucleotide, or single-stranded nucleic acid molecule attached to a solid phase support is attached through a linker moiety.

51. The method of generating a single-stranded nucleic acid molecule according to claim 50, wherein the linker moiety is selected from a phosphate linker and an amine linker.

52. The method of generating a single-stranded nucleic acid molecule according to claim 28, further comprising amplifying the single-stranded nucleic acid molecule by the polymerase chain reaction.

53. The method of generating a single-stranded nucleic acid molecule according to claim 28, further comprising adding a competimer that competes with the template oligonucleotide in step (b).

54. The method of generating a single-stranded nucleic acid molecule according to claim 1, wherein the concentration of each subsequent template oligonucleotide is greater than the concentration of the previous template nucleotide used to form the extension polynucleotide.

* * * * *

SEQUENCE LISTING

<160> NUMBER OF SEQ ID NOS: 40

<210> SEQ ID NO 1
<211> LENGTH: 23
<212> TYPE: DNA
<213> ORGANISM: Artificial
<220> FEATURE:
<223> OTHER INFORMATION: initial polynucleotide

<400> SEQUENCE: 1
tgtaaaacga cggccagtag cct                                       23

<210> SEQ ID NO 2
<211> LENGTH: 54
<212> TYPE: DNA
<213> ORGANISM: artificial
<220> FEATURE:
<223> OTHER INFORMATION: first template oligonucleotide

<400> SEQUENCE: 2
atgtgagtgt gcagtttcag tttatcaatt caggctactg gccgtcgttt taca    54

```
<210> SEQ ID NO 3
<211> LENGTH: 55
<212> TYPE: DNA
<213> ORGANISM: artificial
<220> FEATURE:
<223> OTHER INFORMATION: first exension polynucleotide

<400> SEQUENCE: 3
tgtaaaacga cggccagtag cctgaattga taaactgaaa ctgcacactc acata       55

<210> SEQ ID NO 4
<211> LENGTH: 50
<212> TYPE: DNA
<213> ORGANISM: artificial
<220> FEATURE:
<223> OTHER INFORMATION: first extension polynucleotide and second
      template oligonucleotide

<400> SEQUENCE: 4
ttaacagaat tggtagataa tatgcagata attatgtgag tgtgcagttt             50

<210> SEQ ID NO 5
<211> LENGTH: 87
<212> TYPE: DNA
<213> ORGANISM: artificial
<220> FEATURE:
<223> OTHER INFORMATION: second extension polyncleotide

<400> SEQUENCE: 5
tgtaaaacga cggccagtag cctgaattga taaactgaaa ctgcacactc acataattat  60
ctgcatatta tctaccaatt ctgttaa                                      87

<210> SEQ ID NO 6
<211> LENGTH: 87
<212> TYPE: DNA
<213> ORGANISM: artificial
<220> FEATURE:
<223> OTHER INFORMATION: extension template oligonucleotide

<400> SEQUENCE: 6
ttaacagaat tggtagataa tatgcagata attatgtgag tgtgcagttt cagtttatca  60
attcaggcta ctggccgtcg ttttaca                                      87

<210> SEQ ID NO 7
<211> LENGTH: 50
<212> TYPE: DNA
<213> ORGANISM: artificial
<220> FEATURE:
<223> OTHER INFORMATION: third template oligonucleotide

<400> SEQUENCE: 7
aataggaggt tagatgcaga tagtgaaggg ttttaacaga attggtagat             50

<210> SEQ ID NO 8
<211> LENGTH: 119
<212> TYPE: DNA
<213> ORGANISM: artificial
<220> FEATURE:
<223> OTHER INFORMATION: third extension polynucleotide

<400> SEQUENCE: 8
tgtaaaacga cggccagtag cctgaattga taaactgaaa ctgcacactc acataattat  60
ctgcatatta tctaccaatt ctgttaaaac ccttcactat ctgcatctaa cctcctatt  119
```

<210> SEQ ID NO 9
<211> LENGTH: 119
<212> TYPE: DNA
<213> ORGANISM: artificial
<220> FEATURE:
<223> OTHER INFORMATION: complement of artificial 8

<400> SEQUENCE: 9
aataggaggt tagatgcaga tagtgaaggg ttttaacaga attggtagat aatatgcaga    60
taattatgtg agtgtgcagt ttcagtttat caattcaggc tactggccgt cgttttaca   119

<210> SEQ ID NO 10
<211> LENGTH: 50
<212> TYPE: DNA
<213> ORGANISM: artificial
<220> FEATURE:
<223> OTHER INFORMATION: template oligonucleotides

<400> SEQUENCE: 10
aataagaaca gatacagtaa attataagca gtaataggag gttagatgca                50

<210> SEQ ID NO 11
<211> LENGTH: 50
<212> TYPE: DNA
<213> ORGANISM: artificial
<220> FEATURE:
<223> OTHER INFORMATION: template oligonucleotides

<400> SEQUENCE: 11
cagatttagt tggaggttat cagttaggat ataataagaa cagatacagt                50

<210> SEQ ID NO 12
<211> LENGTH: 50
<212> TYPE: DNA
<213> ORGANISM: artificial
<220> FEATURE:
<223> OTHER INFORMATION: template oligonucleotides

<400> SEQUENCE: 12
gtatgtatga gacagattgg gtgatataaa gtcagattta gttggaggtt                50

<210> SEQ ID NO 13
<211> LENGTH: 50
<212> TYPE: DNA
<213> ORGANISM: artificial
<220> FEATURE:
<223> OTHER INFORMATION: template oligonucleotides

<400> SEQUENCE: 13
gagtcagtta cagaatgatg aatgcagtta ttgtatgtat gagacagatt                50

<210> SEQ ID NO 14
<211> LENGTH: 50
<212> TYPE: DNA
<213> ORGANISM: artificial
<220> FEATURE:
<223> OTHER INFORMATION: template oligonucleotides

<400> SEQUENCE: 14
tattagctga attgagcagt tttagggagt ttgagtcagt tacagaatga                50

<210> SEQ ID NO 15
<211> LENGTH: 50
<212> TYPE: DNA
<213> ORGANISM: artificial

```
<220> FEATURE:
<223> OTHER INFORMATION: template oligonucleotides

<400> SEQUENCE: 15
ttaatggaca gtatagttgg tgtaagagca gttattagct gaattgagca                50

<210> SEQ ID NO 16
<211> LENGTH: 50
<212> TYPE: DNA
<213> ORGANISM: artificial
<220> FEATURE:
<223> OTHER INFORMATION: template oligonucleotides

<400> SEQUENCE: 16
cagtttcaga aatggaagag cagaaataga atttaatgga cagtatagtt                50

<210> SEQ ID NO 17
<211> LENGTH: 50
<212> TYPE: DNA
<213> ORGANISM: artificial
<220> FEATURE:
<223> OTHER INFORMATION: template oligonucleotides

<400> SEQUENCE: 17
ttgaggaggg aacagtatga tgggttgtgt gtcagtttca gaaatggaag                50

<210> SEQ ID NO 18
<211> LENGTH: 50
<212> TYPE: DNA
<213> ORGANISM: artificial
<220> FEATURE:
<223> OTHER INFORMATION: template oligonucleotides

<400> SEQUENCE: 18
taatcagtta ggtgaagaaa tttacagttt gtttgaggag ggaacagtat                50

<210> SEQ ID NO 19
<211> LENGTH: 50
<212> TYPE: DNA
<213> ORGANISM: artificial
<220> FEATURE:
<223> OTHER INFORMATION: template oligonucleotides

<400> SEQUENCE: 19
aacagataaa gagaggcaga atgggtatgg tttaatcagt taggtgaaga                50

<210> SEQ ID NO 20
<211> LENGTH: 50
<212> TYPE: DNA
<213> ORGANISM: artificial
<220> FEATURE:
<223> OTHER INFORMATION: template oligonucleotides

<400> SEQUENCE: 20
ggtaatggca gatataggga taggtagtca gtaacagata aagagaggca                50

<210> SEQ ID NO 21
<211> LENGTH: 50
<212> TYPE: DNA
<213> ORGANISM: artificial
<220> FEATURE:
<223> OTHER INFORMATION: template oligonucleotides

<400> SEQUENCE: 21
cagaaattag agttggaaat cagaatttgt ttggtaatgg cagatatagg                50
```

```
<210> SEQ ID NO 22
<211> LENGTH: 50
<212> TYPE: DNA
<213> ORGANISM: artificial
<220> FEATURE:
<223> OTHER INFORMATION: template oligonucleotides

<400> SEQUENCE: 22
gtttatagag tactgatatg gtttgggaag atcagaaatt agagttggaa            50

<210> SEQ ID NO 23
<211> LENGTH: 50
<212> TYPE: DNA
<213> ORGANISM: artificial
<220> FEATURE:
<223> OTHER INFORMATION: template oligonucleotides

<400> SEQUENCE: 23
tgtacagtaa gaaaatggat attacagaat ctgtttatag agtactgata            50

<210> SEQ ID NO 24
<211> LENGTH: 50
<212> TYPE: DNA
<213> ORGANISM: artificial
<220> FEATURE:
<223> OTHER INFORMATION: template oligonucleotides

<400> SEQUENCE: 24
aatgttgtag aaggtgcaga tagattaaga tttgtacagt aagaaaatgg            50

<210> SEQ ID NO 25
<211> LENGTH: 50
<212> TYPE: DNA
<213> ORGANISM: artificial
<220> FEATURE:
<223> OTHER INFORMATION: template oligonucleotides

<400> SEQUENCE: 25
gtatgataca gttattagtg gttgttgaca gtaatgttgt agaaggtgca            50

<210> SEQ ID NO 26
<211> LENGTH: 631
<212> TYPE: DNA
<213> ORGANISM: artificial
<220> FEATURE:
<223> OTHER INFORMATION: long polynucleotide

<400> SEQUENCE: 26
tgtaaaacga cggccagtag cctgaattga taaactgaaa ctgcacactc acataattat   60
ctgcatatta tctaccaatt ctgttaaaac ccttcactat ctgcatctaa cctcctatta  120
ctgcttataa tttactgtat ctgttcttat tatatcctaa ctgataacct ccaactaaat  180
ctgactttat atcacccaat ctgtctcata catacaataa ctgcattcat cattctgtaa  240
ctgactcaaa ctccctaaaa ctgctcaatt cagctaataa ctgctcttac accaactata  300
ctgtccatta aattctattt ctgctcttcc atttctgaaa ctgacacaca acccatcata  360
ctgttccctc ctcaaacaaa ctgtaaattt cttcacctaa ctgattaaac catacccatt  420
ctgcctctct ttatctgtta ctgactacct atccctatat ctgccattac caaacaaatt  480
ctgatttcca actctaattt ctgatcttcc caaaccatat cagtactcta taaacagatt  540
ctgtaatatc cattttctta ctgtacaaat cttaatctat ctgcaccttc tacaacatta  600
ctgtcaacaa ccactaataa ctgtatcata c                                  631
```

```
<210> SEQ ID NO 27
<211> LENGTH: 18
<212> TYPE: DNA
<213> ORGANISM: artificial
<220> FEATURE:
<223> OTHER INFORMATION: synthesis of a long nucleic acid using a
      polymerase extension

<400> SEQUENCE: 27
tgtaaaacga cggccagt                                                   18

<210> SEQ ID NO 28
<211> LENGTH: 50
<212> TYPE: DNA
<213> ORGANISM: artificial
<220> FEATURE:
<223> OTHER INFORMATION: synthesis of a long nucleic acid using a
      polymerase extension

<400> SEQUENCE: 28
tatgtgagtg tgcagtttca gtttatcaat tcactggccg tcgttttaca                50

<210> SEQ ID NO 29
<211> LENGTH: 50
<212> TYPE: DNA
<213> ORGANISM: artificial
<220> FEATURE:
<223> OTHER INFORMATION: synthesis of a long nucleic acid using a
      polymerase extension

<400> SEQUENCE: 29
tgtaaaacga cggccagtga attgataaac tgaaactgca cactcacata                50

<210> SEQ ID NO 30
<211> LENGTH: 50
<212> TYPE: DNA
<213> ORGANISM: artificial
<220> FEATURE:
<223> OTHER INFORMATION: synthesis of a long nucleic acid using a
      polymerase extension

<400> SEQUENCE: 30
ttaacagaat tggtagataa tatgcagata attatgtgag tgtgcagttt                50

<210> SEQ ID NO 31
<211> LENGTH: 82
<212> TYPE: DNA
<213> ORGANISM: artificial
<220> FEATURE:
<223> OTHER INFORMATION: synthesis of a long nucleic acid using a
      polymerase extension

<400> SEQUENCE: 31
tgtaaaacga cggccagtga attgataaac tgaaactgca cactcacata attatctgca     60
tattatctac caattctgtt aa                                              82

<210> SEQ ID NO 32
<211> LENGTH: 50
<212> TYPE: DNA
<213> ORGANISM: artificial
<220> FEATURE:
<223> OTHER INFORMATION: template oligonucleotides

<400> SEQUENCE: 32
aataggaggt tagatgcaga tagtgaaggg ttttaacaga attggtagat                50
```

```
<210> SEQ ID NO 33
<211> LENGTH: 50
<212> TYPE: DNA
<213> ORGANISM: artificial
<220> FEATURE:
<223> OTHER INFORMATION: template oligonucleotides

<400> SEQUENCE: 33
aataagaaca gatacagtaa attataagca gtaataggag gttagatgca          50

<210> SEQ ID NO 34
<211> LENGTH: 50
<212> TYPE: DNA
<213> ORGANISM: artificial
<220> FEATURE:
<223> OTHER INFORMATION: template oligonucleotides

<400> SEQUENCE: 34
cagatttagt tggaggttat cagttaggat ataataagaa cagatacagt          50

<210> SEQ ID NO 35
<211> LENGTH: 50
<212> TYPE: DNA
<213> ORGANISM: artificial
<220> FEATURE:
<223> OTHER INFORMATION: template oligonucleotides

<400> SEQUENCE: 35
gtatgtatga gacagattgg gtgatataaa gtcagattta gttggaggtt          50

<210> SEQ ID NO 36
<211> LENGTH: 50
<212> TYPE: DNA
<213> ORGANISM: artificial
<220> FEATURE:
<223> OTHER INFORMATION: template oligonucleotides

<400> SEQUENCE: 36
gagtcagtta cagaatgatg aatgcagtta ttgtatgtat gagacagatt          50

<210> SEQ ID NO 37
<211> LENGTH: 50
<212> TYPE: DNA
<213> ORGANISM: artificial
<220> FEATURE:
<223> OTHER INFORMATION: template oligonucleotides

<400> SEQUENCE: 37
tattagctga attgagcagt tttagggagt ttgagtcagt tacagaatga          50

<210> SEQ ID NO 38
<211> LENGTH: 50
<212> TYPE: DNA
<213> ORGANISM: artificial
<220> FEATURE:
<223> OTHER INFORMATION: template oligonucleotides

<400> SEQUENCE: 38
ttaatggaca gtatagttgg tgtaagagca gttattagct gaattgagca          50

<210> SEQ ID NO 39
<211> LENGTH: 306
<212> TYPE: DNA
<213> ORGANISM: artificial
<220> FEATURE:
```

-continued

```
<223> OTHER INFORMATION: final extension polynucleotide

<400> SEQUENCE: 39
tgtaaaacga cggccagtga attgataaac tgaaactgca cactcacata attatctgca      60
tattatctac caattctgtt aaaacccttc actatctgca tctaacctcc tattactgct     120
tataatttac tgtatctgtt cttattatat cctaactgat aacctccaac taaatctgac    180
tttatatcac ccaatctgtc tcatacatac aataactgca ttcatcattc tgtaactgac    240
tcaaactccc taaaactgct caattcagct aataactgct cttacaccaa ctatactgtc    300
cattaa                                                                306

<210> SEQ ID NO 40
<211> LENGTH: 16
<212> TYPE: DNA
<213> ORGANISM: artificial
<220> FEATURE:
<223> OTHER INFORMATION: extension oligonucleotide

<400> SEQUENCE: 40
gactgacttt tttttt                                                      16
```